(12) United States Patent
Vandegriff et al.

(10) Patent No.: US 8,609,815 B2
(45) Date of Patent: Dec. 17, 2013

(54) METHODS FOR PREPARING STABLE DEOXYGENATED PEG-HEMOGLOBIN CONJUGATE SOLUTIONS COMPRISING AN ANTIOXIDANT

(75) Inventors: Kim D. Vandegriff, San Diego, CA (US); Ashok S. Malavalli, San Diego, CA (US)

(73) Assignee: Sangart, Inc., San Diego, CA (US)

( * ) Notice: Subject to any disclaimer, the term of this patent is extended or adjusted under 35 U.S.C. 154(b) by 6359 days.

(21) Appl. No.: 13/224,084

(22) Filed: Sep. 1, 2011

(65) Prior Publication Data

US 2012/0059153 A1 Mar. 8, 2012

Related U.S. Application Data

(60) Provisional application No. 61/379,536, filed on Sep. 2, 2010.

(51) Int. Cl.
*A61K 35/14* (2006.01)
*C07K 1/107* (2006.01)

(52) U.S. Cl.
USPC .......................................... 530/385; 530/402

(58) Field of Classification Search
None
See application file for complete search history.

(56) References Cited

U.S. PATENT DOCUMENTS

| | | | |
|---|---|---|---|
| 4,670,417 A | 6/1987 | Iwasaki et al. | |
| 5,051,353 A * | 9/1991 | Stratton et al. | ................... 435/2 |
| 5,234,903 A | 8/1993 | Nho et al. | |
| 5,895,810 A | 4/1999 | Light et al. | |
| 5,929,031 A | 7/1999 | Kerwin et al. | |
| 6,974,794 B1 | 12/2005 | Adamson et al. | |
| 7,005,414 B2 | 2/2006 | Barnikol et al. | |
| 7,435,795 B2 | 10/2008 | McGinnis et al. | |
| 2004/0259769 A1 * | 12/2004 | Looker et al. | ..................... 514/6 |
| 2009/0082257 A1 | 3/2009 | Winslow | |
| 2010/0311657 A1 * | 12/2010 | Abuchowski et al. | ....... 514/13.5 |

* cited by examiner

*Primary Examiner* — Suzanne M Noakes
(74) *Attorney, Agent, or Firm* — Senniger Powers LLP

(57) ABSTRACT

The present invention is a method for preparing stable HBOC solutions. Specifically, the method comprises the steps of deoxygenating a PEG-Hb conjugate and adding one or more antioxidants during or following the deoxygenating step to form a stabilized PEG-Hb conjugate. The Hb in the PEG-Hb conjugate is not crosslinked and the stabilized PEG-Hb conjugate has a p50 less than that of native SFH from the same animal source when measured under the same conditions. Specifically, the p50 is 6±2 mmHg or less than 10 mmHg.

22 Claims, 5 Drawing Sheets

METHODS FOR PREPARING STABLE DEOXYGENATED PEG-HEMOGLOBIN CONJUGATE SOLUTIONS COMPRISING AN ANTIOXIDANT

CROSS-REFERENCE TO RELATED APPLICATIONS

This application claims priority benefit of U.S. Provisional patent application Ser. No. 61/739,536 filed Sep. 2, 2010, which is incorporated by reference in its entirety.

TECHNICAL FIELD

The present invention relates generally to methods for preparing stable hemoglobin based oxygen carrier ("HBOC") solutions. Specifically, the present invention relates to methods for preparing deoxygenated polyethylene glycol-conjugated hemoglobin ("PEG-Hb") solutions comprising antioxidants that have reduced auto-oxidation rates at low and ambient temperatures.

BACKGROUND OF THE INVENTION

Oxygen carriers that are useful as oxygen therapeutics (sometimes referred to as "oxygen-carrying plasma expanders") can be grouped into three categories: i) perfluorocarbon-based emulsions; ii) liposome-encapsulated hemoglobin ("Hb"); and iii) modified Hb. As discussed below, none of these therapeutics have been entirely successful. However, products comprising modified cell-free Hb are thought to be the most promising. Perfluorochemical-based emulsions must be emulsified with a lipid, typically egg-yolk phospholipid, before they can be used in biological systems. Unlike Hb, these emulsions dissolve molecular oxygen rather than binding the oxygen as a ligand. Though the perfluorocarbon emulsions are inexpensive to manufacture, they do not carry sufficient oxygen at clinically tolerated doses to be effective. Conversely, while liposome-encapsulated Hb has been shown to be effective, it is too costly for widespread use. (See generally, Winslow, R. M., "Hemoglobin-based Red Cell Substitutes," Johns Hopkins University Press, Baltimore (1992)).

Initial attempts to use free Hb from erythrocyte hemolysates as a red cell substitute were unsuccessful. The stromal components were found to be toxic, resulting in coagulopathy associated with acute renal failure. In 1967, the first stroma-free Hb ("SFH") solutions had been prepared for use as plasma expanders (Rabiner, S. F. et al., 1967, J. Exp. Med. 126:1127-1142). However, these solutions had a limited transfusion half-life of about 100 minutes.

The reason for the short circulation half-life of SFH is due to the ability of the tetrameric protein to dissociate into dimers, which are rapidly filtered from the circulation by the kidneys. Accordingly, a multitude of methods for cross-linking Hb to retain its tetrameric structure were devised. U.S. Pat. No. 5,296,465 describes intramolecular cross-linking to prevent dimer formation. Cross-linking Hb may be achieved with diaspirin (diesters of bis-3,5-dibromosaliocylate, U.S. Pat. No. 4,529,719) or 2-N-2-formyl-pyridoxal-5'-phosphate and borohydride (Benesch, R. E. et al., 1975, Biochem. Biophys. Res. Commun. 62:1123-1129). In addition, Simon, S. R. and Konigsberg, W. H. (1966, PNAS 56:749-56) disclosed the use of bis-(N-maleimidomethyl)ether ("BME") to generate intramolecularly cross-linked Hb that was reported to have a four-fold increase in half-life when infused into rats and dogs (Bunn, H. F. et al., 1969, J. Exp. Med. 129:909-24). However, the cross-linking of Hb with BME resulted in the concomitant increase in the oxygen affinity of Hb, which at the time was thought to prevent its use as a potential HBOC.

In addition, methods for conjugating Hb to macromolecules were developed to increase hydrodynamic size and limit or prevent extravasation. Cross-linking SFH to form poly-Hb is described in U.S. Pat. Nos. 4,001,200 and 4,001,401. SFH was also linked to other macromolecules such as dextran (Chang, J. E. et al., 1977, Can. J. Biochem. 55:398-403), hydroxyethyl starch (DE 2,161,086), gelatin (DE 2,449,885), albumin (DE 2,449,885) and PEG (DE 3,026,398 and U.S. Pat. Nos. 4,670,417, 4,412,989 and 4,301,144).

Some of the physiological effects of these oxygen-carrying solutions are not fully understood. Perhaps the most controversial effect is the propensity to cause vasoconstriction, which can manifest as hypertension in animals and man (Amberson, W., 1947, Science 106:117-117 and Keipert, P. et al., 1993, Transfusion 33:701-708). One of the first red cell substitutes developed by the U.S. Army was human Hb cross-linked between α-chains with bis-dibromosalicyl-fumarate ("ααHb"). However, ααHb was abandoned after it showed severe increases in pulmonary and systemic vascular resistance (Hess, J. et al., 1991, Blood 78:356A). A commercial version of this cross-linked Hb was also abandoned after a disappointing Phase III clinical trial (Winslow, R. M., 2000, Vox Sang 79:1-20).

The most commonly advanced explanation for the vasoconstriction produced by cell-free Hb is that it readily binds the endothelium-derived relaxing factor, nitric oxide ("NO"). Two molecular approaches have been advanced in attempting to overcome the NO binding activity of Hb. The first approach attempted to reduce the NO binding by modifying the distal heme pocket through site-specific mutagenesis (Eich, R. F. et al., 1996, Biochem. 35:6976-83). The second approach attempted to reduce or inhibit extravasation of Hb by increasing its molecular size (Hess, J. R. et al., 1978, J. Appl. Physiol. 74:1769-78, Muldoon, S. M. et al., 1996, J. Lab. Clin. Med. 128:579-83, Macdonal, V. W. et al., 1994, Biotechnology 22:565-75, Furchgott, R., 1984, Ann. Rev. Pharmacol. 24:175-97 and Kilbourne, R. et al., 1994, Biochem. Biophys. Res. Commun. 199:155-62).

Recombinant Hbs with reduced NO affinity have been produced that are less hypertensive in top-load rat experiments (Doherty, D. H. et al., 1998, Nature Biotechnology 16:672-676 and Lemon, D. D. et al., 1996, Biotech 24:378). However, studies suggest that NO binding is not the only explanation for the vasoactivity of Hb. Specifically, certain large Hb molecules, such as those modified with PEG, were virtually free of the hypertensive effect, even though their NO binding rates were identical to those of ααHb (Rohlfs, R. J. et al., 1998, J. Biol. Chem. 273:12128-12134). In addition, PEG modified Hb was extraordinarily effective in preventing the consequences of hemorrhage when given as an exchange transfusion prior to hemorrhage (Winslow, R. M. et al., 1998, J. Appl. Physiol. 85:993-1003).

The conjugation of PEG to Hb reduces antigenicity and extends circulation half-life of the Hb. However, the PEG-conjugation reaction has been reported to result in dissociation of Hb tetramers into monomer subunits. These low molecular weight monomeric PEG-Hb conjugates caused gross hemoglobinuria when transfused into rats (Iwashita and Ajisaka, Organ-Directed Toxicity Chem. Indices Mech., Proc. Symp., Brown et al., 1981, Eds. Pergamon, Oxford, England pgs 97-101). A polyalkylene oxide ("PAO") conjugated Hb, having a molecular weight greater than 84,000 Da, was prepared by Enzon, Inc. (U.S. Pat. No. 5,650,388). The conjugate contained ten PEG-5,000 chains linked to Hb at its α- and ε-amino groups. This degree of substitution was described as avoiding hemoglobinuria and associated nephrotoxicity in mammals. However, the conjugation reaction resulted in a heterogeneous conjugate population and contained other undesirable reactants that had to be removed by column chromatography.

PEG conjugation is typically performed by reacting activated PEG with functional groups on the surface of biomolecules. The most common functional groups in a biomolecule are: the amino groups of lysine and histidine residues, thiol groups of cysteine residues, and the hydroxyl groups of serine, threonine and tyrosine residues. The N- and C-termini of the biomolecule may also act as active functional groups. PEG is usually activated by converting the hydroxyl terminus to a moiety capable of reacting with these functional groups in a mild aqueous environment. One of the most common PEGs used for conjugation of therapeutic biopharmaceuticals is methoxy-PEG ("mPEG"). Methoxy-PEG has only one functional group (i.e. hydroxyl), which minimizes cross-linking and aggregation problems that are associated with bifunctional PEG. However, mPEG is often contaminated with high molecular weight PEG (i.e. "PEG diol"). The contamination problem is the result of the production process and is further aggravated as the molecular weight of the PEG increases. In mPEG the amount of contaminant can range as high as 10 to 15% (Dust, J. M. et al., 1990, Macromolecule 23:3742-3746) due to its production process. The purity of mPEG is especially critical for the production of PEG conjugated biotherapeutics because the FDA requires a high level of reproducibility in the production processes and quality of the final product.

A variety of linkers and methods have been developed for conjugating macromolecules to Hb. Phenyl linkers, such as 4-phenylmaleimido or 3-phenylmaleimido (U.S. Pat. No. 5,750,725) and isothiocyanophenylcarbamate (U.S. Pat. No. 7,144,989) have been used to conjugate PEG-5,000 to Hb. However, the use of phenyl groups in a blood substitute is believed by some to be undesirable. To avoid the use of phenyl linkers, succinimidyl activated PEG was prepared for binding free ε-amines available on the surface of Hb (Larwood, D. J. and Szoka, F. C., 1984, J. Labeled Compounds Radiopharm. 21:603-14). However, the ester bond formed between PEG and the succinimidyl group is easily hydrolyzed in the body. To address this issue, activated PAOs having reactive moieties that produce urethane linkages with ε-amino groups of Hb were developed. The urethane linkages are less susceptible to hydrolytic degradation in the circulatory system (U.S. Pat. No. 5,234,903). Other methods have been utilized that employ thiolation of the ε-amines of Hb for binding maleimide activated PAOs (U.S. Pat. No. 6,844,317). The thioester bonds formed under these methods are less susceptible to degradation (U.S. Pat. App. No. 2006/0135753).

Conjugation of Hb to PAOs has been performed in both the oxygenated and deoxygenated states. U.S. Pat. No. 6,844,317 describes conjugating Hb in the oxygenated, or "R" state, to enhance the oxygen affinity of the resultant PEG-Hb conjugate. This is accomplished by equilibrating Hb with the atmosphere before conjugation. Others describe a deoxygenation step prior to conjugation to diminish the oxygen affinity and increase structural stability. The increased stability enables the Hb to withstand the physical stresses of chemical modification, diafiltration and/or sterile filtration and sterilization (U.S. Pat. No. 5,234,903). Deoxygenating Hb prior to modification has also been suggested for efficient intramolecular cross-linking. U.S. Pat. No. 5,234,903 discloses that deoxygenation is required to expose lysine 99 of the α-chain for intramolecular cross-linking.

Stability of HBOCs for storage is currently under investigation. Susceptibility to autoxidation and the formation of MetHb may hinder the clinical use of HBOCs. Formation of MetHb in the circulation can be deleterious for a number of reasons. MetHb does not bind oxygen. Consequently, its formation decreases the oxygen carrying capacity of blood. The presence of MetHb in the blood gives rise to reactive oxygen species "ROS", which may play a role in the development of oxidative damage in vivo (Reeder, B. J. et al., 2004, Antioxid. Redox Signal 6:941-943). In addition, the chemical bond that stabilizes the heme in native Hb is weakened in MetHb. This destabilization allows the heme to be released more quickly, thereby giving rise to a cascade of effects, including induction of heme oxygenase-1 (Balla, G. et al., 1993, PNAS 90:9280-9284 and Motterlini, R. et al., 1995, Am. J. Physiol. 269: H648). In whole blood, oxidation is made reversible by an effective redox system catalyzed by NADPH-dependent MetHb reductase. Unfortunately, isolated Hb does not benefit from this defense mechanism. It has been shown, however, that red blood cells in vitro and in the presence of ascorbate have reduced the formation of extracellular MetHb (McGown, E. L. et al., 1990, Biochem. Biophys. Acta 1036: 202-206).

In contrast, it was recently found that the antioxidant ascorbate rapidly oxidized PEG-Hb (Vandegriff, K. D. et al., 2006, Biochem. J. 399:463-471). Other investigations have used antioxidants to stabilize polymerized Hb compositions under deoxygenated conditions (U.S. Pat. Nos. 5,895,810 and 7,435,795). However, to date, antioxidants have not been successful in reducing or preventing auto-oxidation of HBOC's.

Accordingly, there is a need for a method of preparing deoxygenated PEG-Hb conjugates having reduced autoxidation rates when stored at low or ambient temperatures.

SUMMARY OF THE INVENTION

The present invention is a method for preparing stable HBOC solutions. Specifically, the method comprises the steps of deoxygenating a PEG-Hb conjugate and adding one or more antioxidants during or following the deoxygenating step to form a stabilized PEG-Hb conjugate. The resulting stabilized PEG-Hb conjugate has a p50 less than that of native SFH from the same animal source, when measured under the same conditions. Specifically, the p50 is 6±2 mmHg or less than 10 mmHg. In addition, the stabilized PEG-Hb conjugate comprises an average of 7.1 to 8.9 PEG molecules per Hb having a molecular weight of 5,000 g/mol. Further, the Hb in the stabilized PEG-Hb conjugate is not cross-linked.

In one embodiment, the stabilized PEG-Hb conjugate is stable at a variety of temperatures ranging from 0° C. to 45° C. Specifically, 4° C., 25° C. and 40° C. when stored under deoxygenated conditions. The stabilized PEG-Hb conjugate is also stable for periods ranging from one to twenty-four months. Specifically, for at least three months, six months and one-year.

In another embodiment, the one or more antioxidants have a redox potential of less than −0.30V and include N-acetyl cysteine ("NAC") and NADPH.

Other aspects of the invention are found throughout the specification.

DETAILED DESCRIPTION OF THE INVENTION

Figure 1:
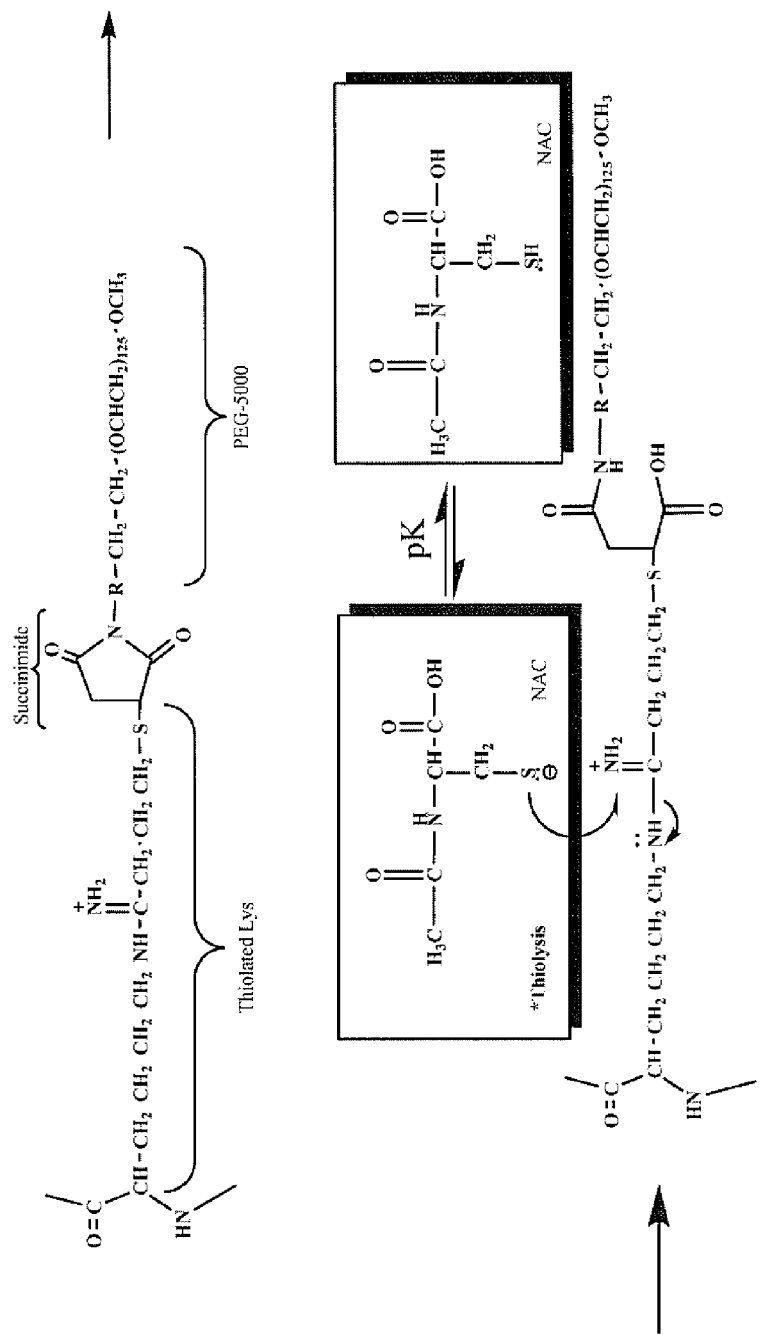
FIG. 1 depicts a thiolysis reaction wherein PEG is removed from a PEG conjugated protein, such as PEG-Hb, with NAC. This is termed residual PEG.

The present invention relates generally to methods for preparing stable HBOC solutions. Specifically, the present invention relates to methods for preparing a stable deoxygenated PEG-Hb conjugate comprising one or more antioxidants to reduce oxidized Hb (MetHb) at low and ambient temperatures.

In the description that follows, a number of terms used in the field of molecular biology, immunology and medicine are extensively utilized. In order to provide a clear and consistent understanding of the specification and claims, including the scope to be given such terms, the following non-limiting definitions are provided.

When the terms "one," "a," or "an" are used in this disclosure, they mean "at least one" or "one or more," unless otherwise indicated.

The term "activated polyalkylene oxide" or "activated PAO" as used herein refers to a PAO molecule that has at least one functional group. A functional group is a reactive moiety that interacts with free amines, sulfhydryls or carboxyl groups on a molecule forming a covalent bond. For example, maleimide is a functional group that interacts with free sulfhydryls and succinimide is a functional group that interacts with a free-amines.

The term "hemoglobin" or "Hb" as used herein refers generally to the protein within red blood cells that transports oxygen. Hb by itself refers both to native unmodified Hb as well as modified Hb. Each molecule of Hb has 4 subunits, 2 α-chain subunits and 2 β-chain subunits, which are arranged in a tetrameric structure. Each subunit also contains one heme group, which is the iron-containing center that binds oxygen. Therefore, each Hb molecule can bind 4 molecules of oxygen.

The term "MalPEG-H-b" as used herein refers to Hb bound to maleimidyl-activated PEG. The conjugation is performed by reacting MalPEG with surface thiol groups and, to a lesser extent, amino groups of Hb. Thiol groups are found in cysteine residues present in the amino acid sequence of Hb. They also can be introduced by modifying the amino groups in the Hb amino acid sequence.

The term "methemoglobin" or "MetHb" as used herein refers to an oxidized form of Hb that contains iron in the ferric state. MetHb does not function as an oxygen carrier.

The term "methemoglobin %" as used herein refers to the percentage of oxidized Hb or MetHb to total Hb.

The term "methoxy-PEG" or "mPEG" as used herein refers to PEG wherein the hydrogen of the terminal hydroxyl group is replaced with a methyl (—CH3) group.

The term "modified hemoglobin" or "modified Hb" as used herein refers to, but is not limited to, Hb that has been altered so that it is no longer in the "native" state. The modification may be by recombinant techniques or by a chemical reaction, such as intra- and inter-molecular cross-linking.

The term "oxygen affinity" as used herein refers to the avidity of an oxygen carrier, such as Hb, to bind molecular oxygen. This characteristic is defined by the oxygen equilibrium curve, which relates the degree of saturation of Hb molecules with oxygen (Y-axis) to the partial pressure of oxygen (X-axis). The position of this curve is denoted by the p50 value, which is the partial pressure of oxygen at which the oxygen carrier is half-saturated with oxygen. The p50 value is inversely related to oxygen affinity. Hence, the lower the p50 value, the higher the oxygen affinity. The oxygen affinity of whole blood, as well as components of whole blood, such as red blood cells and Hb, can be measured by a variety of methods known in the art. (See, e.g., Winslow, R. M. et al., 1977, J. Biol. Chem. 252:2331-2337). Oxygen affinity may also be determined using a commercially available HEMOX™ Analyzer (TCS Scientific Corporation, New Hope, Pa.). (See, e.g., Vandegriff, K. D. and Shrager, R. I. "Methods in Enzymology" (Everse et al., eds.) 232:460-485 (1994)).

The term "perfluorocarbons" as used herein refers to synthetic, inert molecules that consist entirely fluorine and carbon atoms. Perfluorocarbons emulsions are under development as blood substitutes because of their ability to dissolve many times more oxygen than equivalent amounts of plasma or water.

The term "plasma expander" as used herein refers to any solution that may be given to treat blood loss.

The term "polyethylene glycol" or "PEG" as used herein refers to polymers of the general chemical formula H(OCH2CH2)n OH, also known as (α-Hydro-ω-hydroxy-poly-(oxy-1,2-ethanediyl), where "n" is greater than or equal to 4. Any PEG formulation, substituted or unsubstituted, is encompassed by this term. PEGs are commercially available in a number of formulations (e.g., Carbowax™ (Dow Chemical, Midland, Mich.) and Poly-G® (Arch Chemicals, Norwalk, Conn.)).

The term "polyethylene glycol-conjugated hemoglobin," "PEG-Hb conjugate," or "PEG-Hb" as used herein refers to Hb that has molecules of PEG covalently bound to its surface.

The term "stroma-free hemoglobin" or "SFH" as used herein refers to Hb that has been isolated from red blood cells. Specifically, SFH is Hb free of red blood cell membrane.

The term "autoxidation" as used herein refers to the process that converts ferrous iron (Fe+2) to ferric iron (Fe+3) in Hb.

The term "thiolation" as used herein refers to a process that increases the number of sulfhydryl groups on a molecule. For example, reacting a protein with 2-iminothiolane ("2-IT") converts free amines on the surface of the protein to sulfhydryl groups.

A. Hemoglobin-Based Oxygen Carriers

A variety of PAO-Hbs that have or demonstrate an oxygen affinity greater than whole blood may be utilized with the present invention. This means that the PAO-Hbs will have a p50 greater than 3, but less than 10 mmHg. These p50 values translate into a higher O2 binding affinity than SFH, which has a p50 of approximately 15 mmHg, and a significantly higher O2 binding affinity than whole blood, which has a p50 of approximately 28 mmHg.

The idea that increasing oxygen affinity of an HBOC over that of whole blood as a method to enhance oxygen delivery to tissues contradicts the widely held belief that modified Hb blood substitutes should have lower oxygen affinities. The previous belief held that HBOCs should have p50s that approximated that of whole blood to effectively release oxygen to tissue. Because of this, many researchers modified Hb with pyridoxyl phosphate to raise the p50 of SFH from 10 mmHg to approximately 22 mmHg.

1. Organic Polymers

In previous studies, it was observed that increasing the molecular size of modified Hb reduced clearance by the kidneys and achieved the desired circulation half-life. Blumenstein, J. et al., determined that this could be achieved at or above a molecular weight of 84,000 Daltons ("Da") ("Blood Substitutes and Plasma Expanders," Alan R. Liss, editors, New York, N.Y., pages 205-212 (1978)). In that study, the authors conjugated dextran of varying molecular weight to Hb. They reported that a conjugate of Hb (having a molecular weight of 64,000 Da) and dextran (having a molecular weight of 20,000 Da) "was cleared slowly from the circulation and negligibly through the kidneys." Further, it was observed that increasing the molecular weight above 84,000 Da did not significantly alter these clearance rates.

The present invention may be utilized with a variety of PAO-Hb conjugates having a molecular weight of at least 84,000 Da. Suitable PAO polymers used in preparing these conjugates include for example, polyethylene oxide (—(CH2 CH2 O)n-), polypropylene oxide (—(CH(CH3)CH2 O)n-) and a polyethylene/polypropylene oxide copolymer (—(CH2 CH2 O)n- (CH(CH3)CH2 O)n-). Other straight or branched chain and optionally substituted synthetic polymers that would be suitable in the practice of the present invention are well known in the medical field.

The most common PAO presently used to modify the surface of Hb is PEG because of its pharmaceutical acceptability and commercial availability. In addition, PEG is available in a variety of molecular weights based on the number of repeating subunits of ethylene oxide (i.e. —OCH2CH2—) within the molecule. Consequently, PEG also provides the flexibility of achieving a desired molecular weight based on the number and size of the PEG molecules conjugated to Hb.

In order to conjugate PAO to Hb, one or both of the terminal end groups of the PAO polymer must first be converted into a reactive functional group. This process is referred to as "activation". In one well known process, PEG-OH is used to prepare PEG-halide, mesylate or tosylate, which is then converted to PEG-amine ("PEG-NH2") by performing a nucleophilic displacement reaction. The displacement reaction can be performed with aqueous ammonia (Zalipsky, S. et al., 1983, Eur. Polym. J. 19:1177-1183), sodium azide or potassium phthalimide. The activated PEG can then be conjugated to a biological molecule through the interaction of the PEG amine group (—"NH2") with a carboxyl group ("—COOH") of the biological molecule.

PEG-NH2 can be further functionalized to conjugate with groups other than —COOH. For example, U.S. Pat. No. 6,828,401 discloses the reaction of PEG-NH2 with maleimide to form mPEG-maleimide. In this reaction, mPEG-OH is reacted with a tosylating reagent (p-toluenesulfonyl chloride) and a base catalyst (triethyleneamine) in the presence of an organic solvent (dichloromethane) to produce mPEG-tosylate. The mPEG-tosylate is then reacted with 28% ammonia water and maleic acid anhydride in an organic solvent mixture of N,N-dimethylacetamide ("DMAc") and N-cyclohexylpyrrolidinone ("CHP") to produce a maleamic acid compound. This compound is then reacted with pentafluorophenyl trifluoroacetate in the presence of dichloromethane to produce the mPEG-maleimide.

In addition, linkers have been used to conjugate PAO to Hb. These linkers do not generally affect the performance of the surface modified Hb. However, rigid linkers are preferred over flexible linkers because they enhance the manufacturing and/or characteristics of the conjugates. Desired rigid linkers include unsaturated aliphatic or aromatic C1 to C6 linker substituents.

2. Hemoglobin

A variety of Hbs may be utilized with the present invention. The Hb may be obtained from animal sources or produced by recombinant techniques. Human Hb is desirable in the present invention and can be obtained from natural sources. Further, the genes of both human $\alpha$- and $\beta$-globin have been both cloned and sequenced (Liebhaber, S. A. et al., 1980, PNAS 77:7054-7058 and Marotta, C. A. et al., 1977, 3. Biol. Chem. 353: 5040-5053). Consequently, human Hb can also be recombinantly engineered. In addition, many recombinantly modified Hbs have been produced using site-directed mutagenesis. Unfortunately, these "mutant" Hb varieties have undesirably high oxygen affinities (e.g., Nagai, K. et al., 1985, PNAS 82:7252-7255).

Native human Hb has a fixed number of amino acid residue side chains that may be accessed for conjugation to maleimide-activated PAO molecules. These are presented in the chart below:

| Residues | Positions |
|---|---|
| $\alpha$-chain | |
| Lys | 7, 11, 16, 40, 56, 60, 61, 90, 99, 127 and 139 |
| Cys | 104 |
| His | 20, 45, 50, 58, 72, 87, 112 and 122 |
| Val | 1 |
| $\beta$-chain | |
| Lys | 8, 17, 59, 61, 65, 66, 82, 95, 120, 132 and 144 |
| Cys | 93 and 112 |
| His | 2, 63, 77, 92, 97, 116, 117, 143 and 146 |
| Val | 1 |

One method to increase the number of available conjugation sites on Hb is to introduce sulfhydryl groups (also known as thiolation), which tend to be more reactive with PEG-Mal than free amines. A variety of methods are known for protein thiolation. In one method, protein free amines are reacted with succinimidyl 3-(2-pyridyldithio) propionate followed by reduction with dithiothreitol ("DTT"), or tris(2-carboxyethyl)phosphine ("TCEP"). This reaction releases the 2-pyridinethione chromophore, which can be used to determine the degree of thiolation. Amines can also be indirectly thiolated by reaction with succinimidyl acetylthioacetate, followed by 50 mM hydroxylamine, or hydrazine at near-neutral pH.

Another method described in U.S. Pat. No. 5,585,484 maintains the positive charge of the amino ($\alpha$- or $\epsilon$-) group of the Hb after conjugation. This method involves amidination of the $\epsilon$-amino groups of Hb by 2-IT to introduce sulfhydryl groups onto the protein. This approach has at least two additional advantages over the previously used succinimidyl chemistry: 1) the high reactivity and selectivity of maleimide groups with sulfhydryl groups facilitates the near quantitative modification of the thiols, with a limited excess of reagents and 2) the thiol group of 2-IT is latent and is generated only in situ as a consequence of the reaction of the reagent with the protein amino groups. These advantages provide one additional benefit. They allow simultaneous incubation of Hb with both the thiolating and PEGylation reagent for surface decoration.

3. Conjugation

The molecular weight of the PAO-Hb may be regulated by the conjugation reaction. Conventional thought suggested that increasing the molar ratios of the reactants would increase the number of PEG molecules bound to Hb. This included both the thiolation process of Hb (i.e. increasing the molar ratio of thiolating agent to Hb) and the conjugation process (i.e. increasing the molar ratio of thiol activated PEG to thiolated Hb). However, these excess molar ratios resulted in the binding of only 6±1 PEG molecules per Hb (see U.S. Pat. No. 7,501,499).

Recently it was determined that a greater number of PAO molecules could be bound to Hb using lower molar ratios of reactants. The number of available thiol groups on Hb, before and after thiolation and after conjugation, was determined using the dithiopyridine colorimetric assay (Ampulski, R. S. et al., 1969, Biochem. Biophys. Acta 32:163-169). Human Hb contains two intrinsic reactive thiol groups at the β93cysteine residues, which was confirmed by the dithiopyridine reaction. After thiolation of SFH with 2-IT, the number of reactive thiol groups increased from two to over seven. In this example, an average of 8 PEG molecules was bound to Hb. This was achieved using a 7.5 molar excess of 2-IT over SFH in the thiolation reaction and a 12 molar excess of PEG-Mal over thiolated Hb in the conjugation reaction.

4. PEG-Hb Conjugate

The PEG-Hb conjugate of the present invention has an oxygen affinity greater than whole blood. This means that the conjugate will have a p50 greater than 3, but less than 10 mmHg. These p50 values translate into a higher O2 binding affinity than SFH, which has a p50 of approximately 15 mmHg and a significantly higher O2 binding affinity than whole blood, which has a p50 of approximately 28 mmHg. It was suggested that increasing oxygen affinity of HBOC, and thereby lowering the p50, could enhance delivery of oxygen to tissues, but that a p50 lower than that of SFH would not be acceptable. See Winslow, R. M. et al., in "Advances in Blood Substitutes" (1997), Birkäuser, eds. Boston, Mass., at page 167, and U.S. Pat. No. 6,054,427. This suggestion contradicts the widely held belief that HBOCs should have lower oxygen affinities similar to that of whole blood. Consequently, many researchers have used pyridoxyl phosphate to raise the p50 of SFH from 10 mmHg to approximately 22 mmHg.

There are a number of scientific approaches to manufacturing HBOCs with high oxygen affinity. Recent studies have identified the β93 cysteine residue as playing an important role in oxygen affinity. The β92 histidine residue, which is the only residue in the β-subunit directly coordinated to the heme iron, is located immediately adjacent the β93 cysteine residue. This β93 cysteine residue forms a salt bridge with the heme that normally stabilizes the low-affinity T-state Hb conformation (Peretz, M. F. et al., 1974, Biochemistry 13:2163-2173). However, attachment of the bulky maleimide group of PEG-Mal to the β93 cysteine displaces this salt bridge and shifts the quaternary conformation towards the R state, resulting in higher O2 affinity (Imai, K. et al., 1973, Biochemistry, 12:798-807). Because of these findings, site-directed mutagenesis has now been performed to manipulate oxygen affinity to the desired level (see, e.g., U.S. Pat. No. 5,661,124). Other approaches are discussed in U.S. Pat. No. 6,054,427.

In previous studies, it was observed that the molecular size of the resultant modified Hb had to be large enough to avoid being cleared by the kidneys and to achieve the desired circulation half-life. Blumenstein, J. et al. (supra), determined that this could be achieved at or above a molecular weight of 84,000 Da. Because of this, the Hb of a number of HBOCs is crosslinked; meaning that the tetrameric hemoglobin units have been chemically bound or intramolecularly crosslinked to prevent dissociation into dimers. A variety of methods are known in the art for intramolecularly crosslinking Hb. Chemical crosslinking reagents include glutaraldehyde (U.S. Pat. No. 7,005,414), polyaldehydes (U.S. Pat. No. 4,857,636), diaspirin (U.S. Pat. No. 4,529,719), pyridoxyl 5'-phosphate (U.S. Pat. No. 4,529,719) and trimesoyl tris(methyl phosphate) (U.S. Pat. No. 5,250,665). Hbs also may be polymerized by intermolecular crosslinking. U.S. Pat. No. 5,895,810 describes obtaining Hb polymers of up to twelve tetramers using the same or multiple crosslinking reagents. Mixtures containing two or more different species of intermolecularly and intramolecularly crosslinked hemoglobin also have been disclosed. Unlike previous methods, the present invention does not crosslink Hb to achieve a desired molecular weight. In contrast, Hbs are conjugated to PAOs to increase their molecular weight.

B. Deoxygenation

Deoxygenation of HBOCs may be performed by any method known in the art. One simple method is to expose the HBOC solution to an inert gas, such as nitrogen, argon or helium. To assure that deoxygenation is relatively homogeneous, the HBOC solution is circulated in this process. Monitoring deoxygenation to attain desired levels may be performed by using a Co-oximeter 682 (Instrument Laboratories). If partial reoxygenation is desired, deoxygenated Hb may be exposed to oxygen or to gas mixture containing oxygen.

Alternatively, gas exchange may be accomplished through a gas-permeable membrane, such as a polypropylene or cellulose acetate membrane. Commercially available gas-exchange devices utilizing these membranes include the Celgard™ polypropylene microporous hollow fiber device from Hoechst-Celanese (Dallas, Tex.) or the Cell-Pharm™ hollow fiber oxygenator from American Laboratory (East Lyme, Conn.). In the Hoechst-Celanese Celgard™ device, oxygenated Hb is deoxygenated by passing an aqueous Hb solution through polypropylene microporous hollow filters at 10-100 ml/min/ft$^2$ while the system is purged with nitrogen at 5-20 psi. The Hb is generally circulated for about 5 to 30 minutes to achieve the desired percentage of deoxyHb. Another method for producing deoxygenated Hb comprises exposing a Hb solution to a chemical reducing agent such as, sodium ascorbate, sodium dithionate and sodium bisulfite. Hb is partially deoxygenated by adjusting the reducing agent concentration, reaction time and temperature. Alternatively, a reducing agent may be used to substantially deoxygenate Hb, and then oxygen may be reintroduced to form a partially deoxygenated product. In one embodiment of the invention, Hb is exposed to a 100 mM concentration of sodium bisulfite for about one hour prior to the addition of antioxidants.

C. Stabilization

There are at least two reactions involved in the stabilization of the PEG-Hb conjugate. The first is the capability of the antioxidant, such a N-acetyl cysteine (NAC) and NAD(P)H, to reduce ferric Hb (MetHb) to ferrous Hb. The second is the ability of these groups to consume O2 in solution. NAC has been observed to perform both these functions. Free O2 is consumed by the formation of a sulfhydryl bridge between two NAC molecules. The by-product, H2O2, is then consumed in a reaction wherein a sulfhydryl bridge is formed between a second pair of NAC molecules. The resulting reaction requires the presence of four NAC molecules with one molecule of oxygen forming two NAC dimers and 2 molecules of water.

Figure 2:
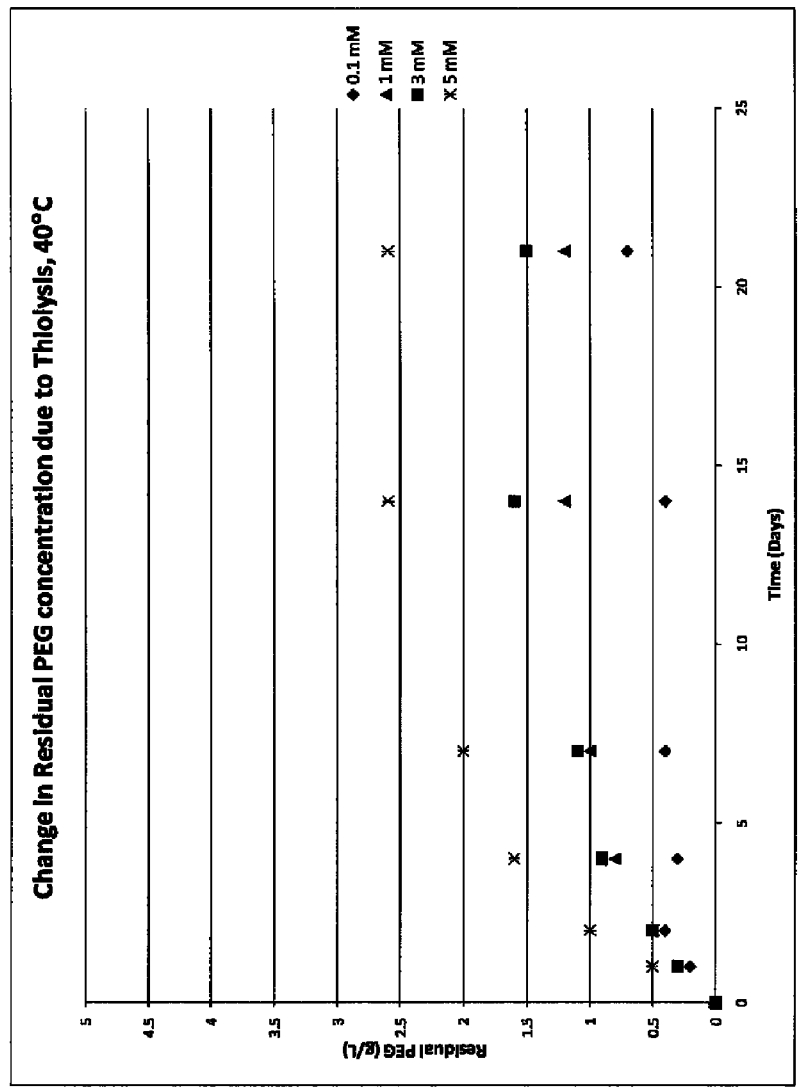
FIG. 2 shows residual PEG formation as a function of NAC concentration at 40° C. over 21 days.

Further studies have indicated that NAC also acts by reducing the sulfhydryl bridging between the PEG and Hb, releasing PEG from the HBOC (FIG. 1). This reaction effectively reduces the molecular weight of the HBOC and increases the concentration of free PEG in solution. Consequently, the use of NAC as an antioxidant for HBOCs prepared via sulfhydryl bridging to polyalkylene oxides has been considered undesirable. However unexpectedly, it was observed that NAC could be utilized as an effective antioxidant when the amount of NAC in solution is just sufficient enough to consume O2 (FIG. 2). This includes the O2 remaining in deoxygenated solution following filling, the concentration of NAC required to reduce any MetHb formed during the deoxygenation process, and O2 that permeates into the storage bag. The method for calculating the amount of NAC sufficient to consume oxygen and not reduce PEG-Hb sulfhydryl bonds is provided in the examples.

NAD(P)H is another antioxidant that has been known for many years to act as a hydride (hydrogen anion) donor in a variety of enzymatic processes. One example is the re-reduction of glutathione disulfide ("GSSG") to GSH, catalyzed by glutathione reductase, similar to the reaction performed by NAC. Because of this, NADPH has been considered to be an indirect antioxidant; by maintaining the antioxidative power of glutathione. Recently published data, (Kirsch, M. and De Groot, H., 2001, FASEB, J. 15:1569-1574), has demonstrated that NADPH and NADH operate as antioxidants.

EXAMPLES

Example 1

Calculation of the Amount of NAC Needed to Stabilize a Deoxygenated Peg-Hb Conjugate Formulation A. Concentration of NAC necessary to remove residual $O_2$ in the deoxygenated PEG-Hb conjugate formulation The following calculation determines the molarity of NAC needed to remove residual O2 in a 250 mL volume of a deoxygenated PEG-Hb conjugate formulation. The stoichiometry of O2 consumption by NAC is 4:1, (i.e. 4 molecules of NAC are required to consume 1 molecule of O2, (Ehrenberg et al., 1989, Acta Chemica Scandinavica 43:177-187)). For this example, the PEG-Hb conjugate formulation is 99% deoxygenated, has a Hb concentration of 4.3 g/dL, and a 15% concentration of PEG-MetHb. The remaining PEG-Hb conjugate is oxygenated. The concentration of heme binding sites in the formulation is 2.27 mM because the 15% PEG-MetHb provides no O2 binding sites (i.e. 2.67 mM heme binding sites in 4.3 g/dL×0.85 available sites=2.27 mM O2 binding sites). Residual O2 concentration in a PEG-Hb conjugate formulation having 1% oxyPEG-Hb conjugate would be approximately 0.023 mM (i.e. 2.27 mM×0.01=0.023 mM O2). Therefore, a 0.1 mM concentration of NAC would be required to consume O2 in the PEG-Hb conjugate formulation (i.e. 0.023 mM O2×4 NAC/O2=0.1 mM NAC).

B. Concentration of NAC Necessary to Reduce Residual MetHb

In this example, the formulation contains 15% MetPEG-Hb. The stoichiometry of reducing MetPEG-Hb by NAC is assumed to be 1:1. Consequently, the concentration of NAC needed to reduce residual MetHb would be 0.4 mM (i.e. 2.67 mM heme binding sites×0.15=0.4 mM NAC).

Consequently, the concentration of NAC required to consume oxygen from a PEG-Hb formulation that is 99% deoxygenated with 15% MetPEG-Hb would be approximately 0.5 mM NAC (i.e. 0.1 mM to remove residual oxyPEG-Hb+0.4 mM to reduce the MetPEG-Hb=0.5 mM NAC total).

Example 2

Reduction in Thiolysis

Figure 3:
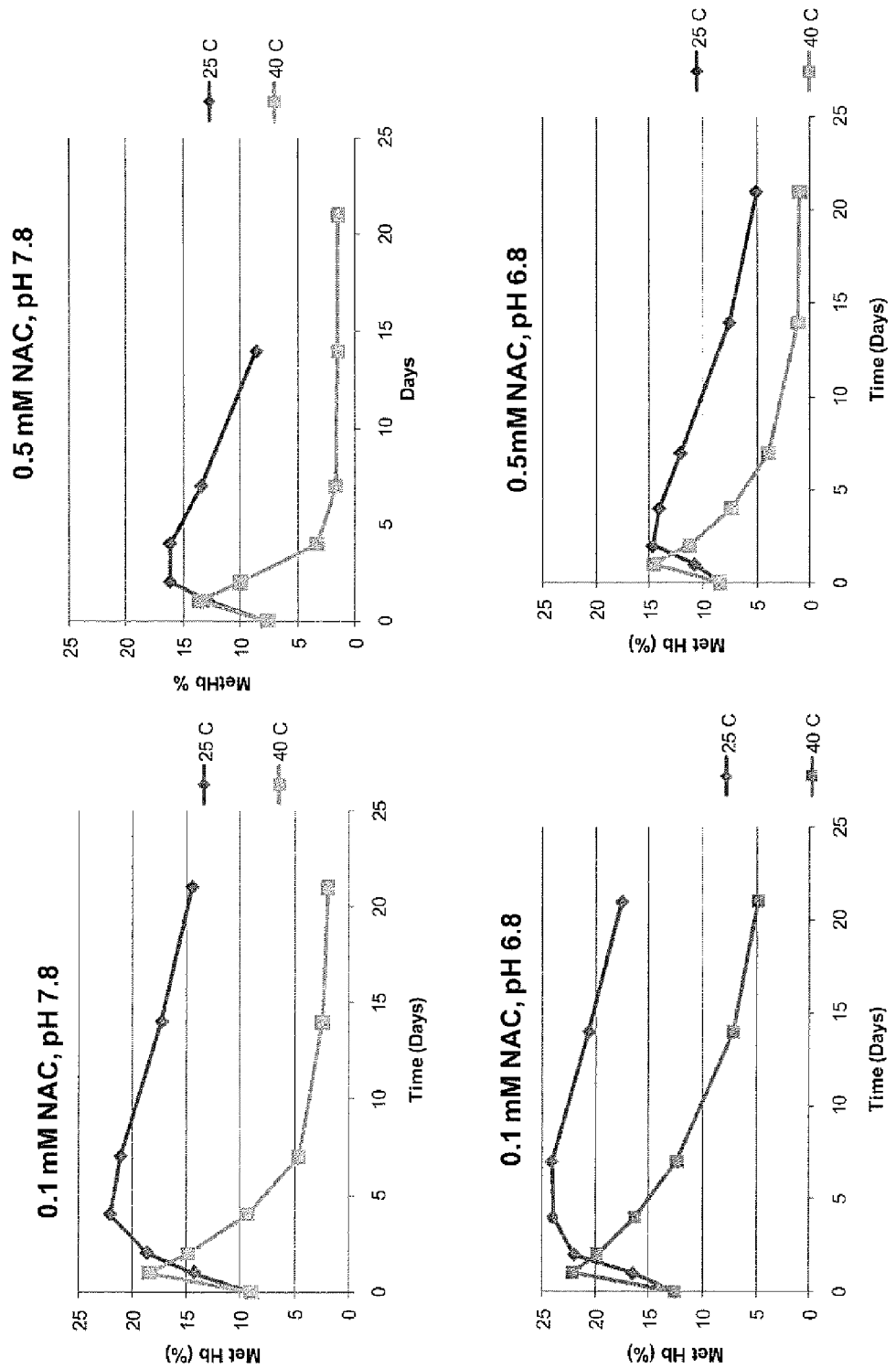
FIG. 3 is a graph of the reduction in MetHb in the PEG-Hb conjugate formulation initially containing either 0.1 or 0.5 mM NAC under storage conditions of 25° C. or 40° C. at either pH 6.8 or 7.8 over 21 days.
Figure 4:
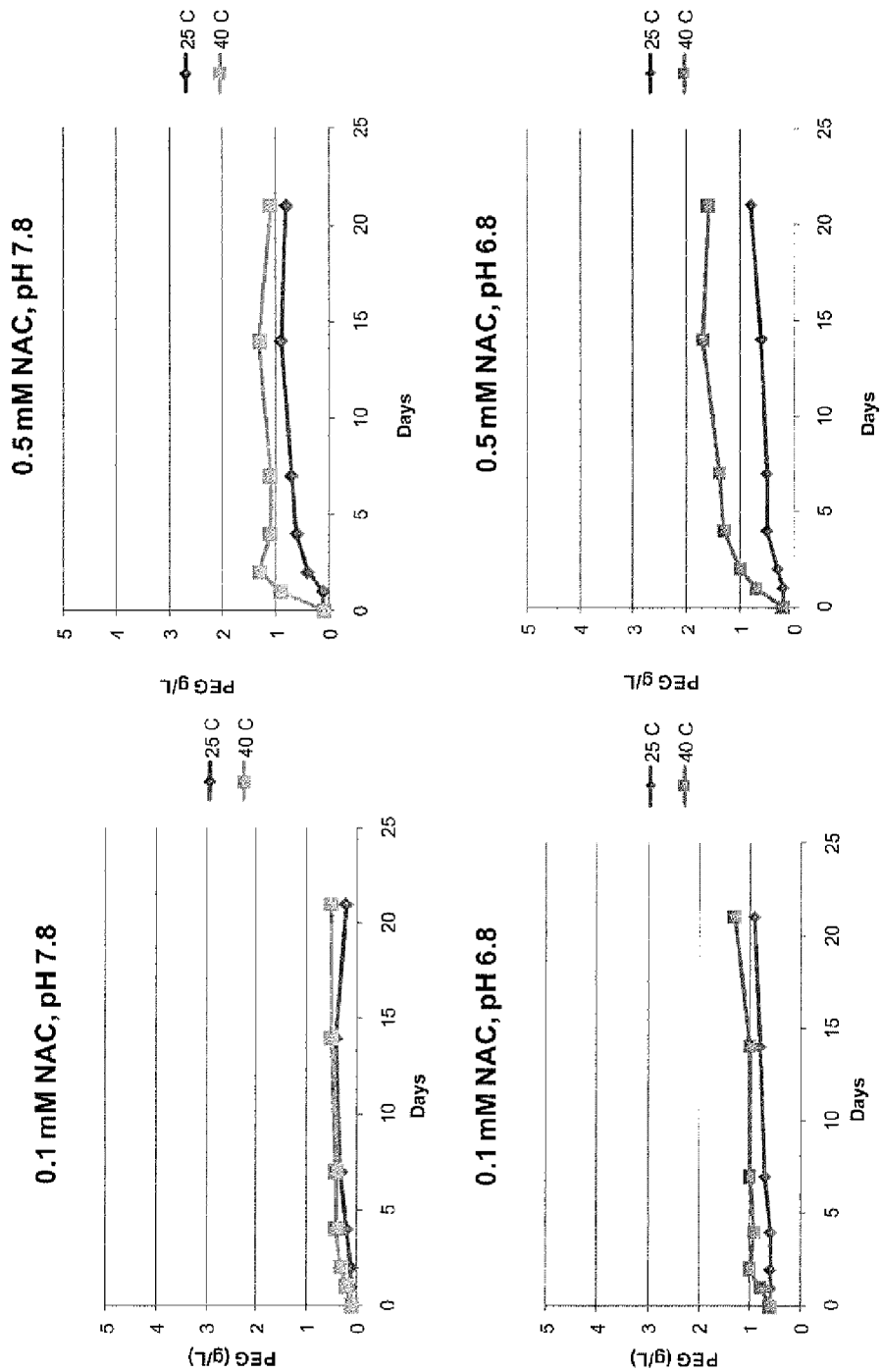
FIG. 4 is a graph of the formation of residual PEG in the PEG-Hb conjugate formulation initially containing either 0.1 or 0.5 mM NAC under storage conditions of 25° C. or 40° C. at either pH 6.8 or 7.8 over 21 days.
Figure 5:
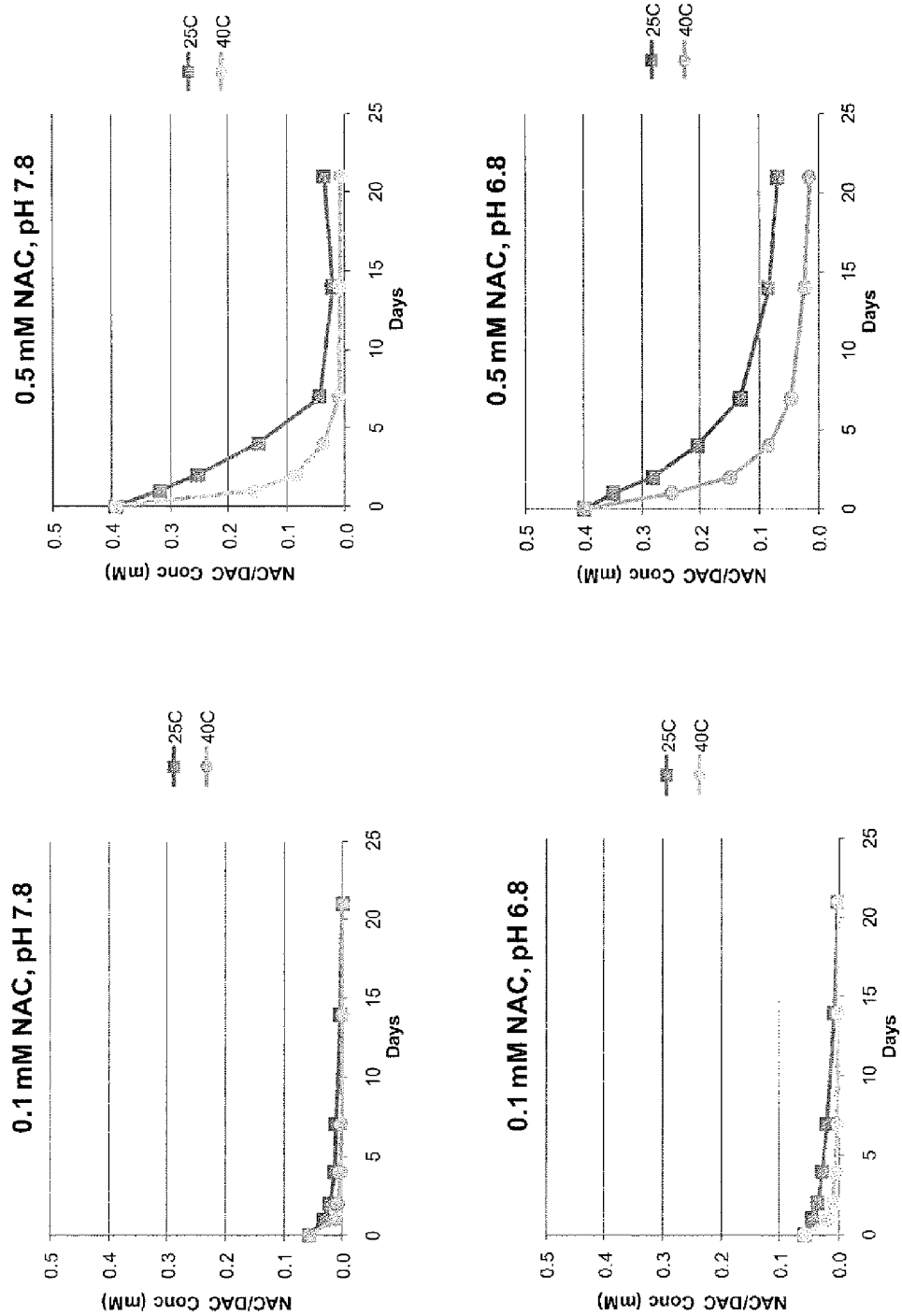
FIG. 5 is a graph of the disappearance or consumption of NAC from the PEG-Hb conjugate formulation containing initially either 0.1 or 0.5 mM NAC under storage conditions of 25° C. or 40° C. at either pH 6.8 or 7.8 over 21 days

The thiolysis of PEG from the PEG-Hb conjugate in the presence of NAC cannot be eliminated only reduced. In this example, a deoxygenated PEG-Hb conjugate was produced at either pH 7.8 or 6.8, with either initial concentrations of NAC at 0.1 or 0.5 mM The samples were then stored at either 25° C. or 40° C. The samples were tested for percent MetHb (FIG. 3), residual PEG (FIG. 4), and NAC concentrations (FIG. 5) over 21 days.

From these observations, the degree of thiolysis is observed to be temperature and NAC concentration dependent. The methods of the present invention allow for a PEG-Hb formulation to be deoxygenated and stored at room or higher temperature, with a reduction in MetHb species, minimization of residual formed PEG, and consumption of NAC over time.

We claim:

1. A method of making a polyethylene glycol hemoglobin (PEG-Hb) conjugate solution comprising the steps of:
   deoxygenating a PEG-Hb conjugate; and
   adding one or more antioxidants during or following the deoxygenating step to form the PEG-Hb conjugate solution;
   wherein PEG-Hb conjugate has a p50 less than 15 mmHg and the PEG-Hb conjugate solution contains less than 10% methemoglobin after storage at 4° C., 25° C. or 40° C. for at least six months under deoxygenated conditions.

2. The method according to claim 1, wherein the PEG-Hb conjugate solution contains less than 10% methemoglobin after storage at 4° C. when stored for at least six months under deoxygenated conditions.

3. The method according to claim 1, wherein the PEG-Hb conjugate solution contains less than 10% methemoglobin after storage at 25° C. when stored for at least six months under deoxygenated conditions.

4. The method according to claim 1, wherein the PEG-Hb conjugate solution contains less than 10% methemoglobin after storage at 40° C. when stored for at least six months under deoxygenated conditions.

5. The method according to claim 1, wherein the PEG-Hb conjugate solution contains less than 10% methemoglobin after storage for at least one year when stored under deoxygenated conditions.

6. The method according to claim 3, wherein the PEG-Hb conjugate solution contains less than 10% methemoglobin after storage for at least one year when stored under deoxygenated conditions.

7. The method according to claim 4, wherein the PEG-Hb conjugate solution contains less than 10% methemoglobin after storage for at least one year when stored under deoxygenated conditions.

8. The method according to claim 1, wherein the PEG-Hb conjugate comprises an average of 8 PEG molecules per hemoglobin.

9. The method according to claim 1, wherein the polyethylene glycol (PEG) in the PEG-Hb conjugate has a molecular weight of 5,000 g/mol.

10. The method according to claim 1, wherein the one or more antioxidants is N-acetyl cysteine (NAC).

11. The method according to claim 1, wherein the one or more antioxidants is nicotinamide adenine dinucleotide phosphate (NADPH).

12. The method according to claim 1, wherein the PEG-Hb conjugate has a p50 of less than 10 mmHg.

13. The method according to claim 1, wherein the PEG-Hb conjugate has a p50 of about 6±2 mmHg.

14. The method according to claim 1, wherein the PEG-Hb conjugate comprises an average of 7.1 to 8.9 PEG molecules per hemoglobin.

15. A composition comprising a polyethylene glycol hemoglobin (PEG-Hb) conjugate having a p50 less than 15 mmHg, and one or more antioxidants in solution, the composition containing less than 10% methemoglobin after storage at 4° C., 25° C. or 40° C. for at least six months under deoxygenated conditions, and being prepared by the method of claim 1.

16. The composition according to claim 15, wherein the PEG-Hb conjugate solution contains less than 10% methemoglobin after storage at 4° C. when stored for at least six months under deoxygenated conditions.

17. The composition according to claim 15, wherein the PEG-Hb conjugate solution contains less than 10% methemoglobin after storage at 25° C. when stored for at least six months under deoxygenated conditions.

18. The composition according to claim 15, wherein the PEG-Hb conjugate solution contains less than 10% methemoglobin after storage at 40° C. when stored for at least six months under deoxygenated conditions.

19. The composition according to claim 15, wherein the PEG-Hb conjugate solution contains less than 10% methemoglobin after storage for at least one year when stored under deoxygenated conditions.

20. The composition according to claim 17, wherein the PEG-Hb conjugate solution contains less than 10% methemoglobin after storage for at least one year when stored under deoxygenated conditions.

21. The composition according to claim 18, wherein the PEG-Hb conjugate solution contains less than 10% methemoglobin after storage for at least one year when stored under deoxygenated conditions.

22. The composition according to claim 15, wherein the PEG-Hb conjugate comprises an average of 7.1 to 8.9 PEG molecules per hemoglobin.

* * * * *